United States Patent
Metro

[19]

[11] Patent Number: 6,090,040

[45] Date of Patent: Jul. 18, 2000

[54] PERISCOPE AND RETRACTING LARYNGOSCOPE FOR INTUBATION

[76] Inventor: R. J. Metro, 139 Elmerston, Rochester, N.Y. 14620

[21] Appl. No.: 09/151,116

[22] Filed: Sep. 10, 1998

[51] Int. Cl.[7] ................................................. A61B 1/267
[52] U.S. Cl. ........................... 600/196; 600/190; 600/195; 600/199
[58] Field of Search ..................................... 600/120, 185, 600/188, 190, 194, 195, 196, 199, 237, 238, 239, 240, 241

[56] References Cited

U.S. PATENT DOCUMENTS

| | | |
|---|---|---|
| 3,669,098 | 6/1972 | Takahashi . |
| 3,677,262 | 7/1972 | Zukowski . |
| 4,086,919 | 5/1978 | Bullard . |
| 4,114,609 | 9/1978 | Moses ...................................... 600/193 |
| 4,306,547 | 12/1981 | Lowell . |
| 4,337,761 | 7/1982 | Upsher . |
| 4,580,556 | 4/1986 | Kondur ................................... 600/120 |
| 4,742,819 | 5/1988 | George . |
| 4,793,327 | 12/1988 | Frankel . |
| 4,827,910 | 5/1989 | Mathews, III . |
| 4,846,153 | 7/1989 | Berci . |
| 4,982,729 | 1/1991 | Wu . |
| 5,092,314 | 3/1992 | Zeitels ..................................... 600/194 |
| 5,178,132 | 1/1993 | Mahefky . |
| 5,261,392 | 11/1993 | Wu ......................................... 600/194 |
| 5,287,848 | 2/1994 | Cubb et al. . |
| 5,327,881 | 7/1994 | Greene . |
| 5,339,805 | 8/1994 | Parker ................................. 128/200.26 |
| 5,402,771 | 4/1995 | Pilling ....................................... 600/188 |
| 5,431,152 | 7/1995 | Flam et al. . |
| 5,498,231 | 3/1996 | Franicevic . |
| 5,558,082 | 9/1996 | Spencer .............................. 128/200.26 |
| 5,607,386 | 3/1997 | Flam . |
| 5,893,830 | 4/1999 | Zeitels ..................................... 600/185 |

FOREIGN PATENT DOCUMENTS

| | | | |
|---|---|---|---|
| 1329-768 | 8/1987 | U.S.S.R. .............................. 600/188 |
| 2189148 | 10/1987 | United Kingdom ................... 600/185 |

*Primary Examiner*—Linda C. M. Dvorak
*Assistant Examiner*—Brad C. Blaise
*Attorney, Agent, or Firm*—Harter, Secrest & Emery LLP; Stephen B. Salai, Esq.; Brian B. Shaw, Esq.

[57] ABSTRACT

Instrumentation comprising an automatic positioning and retracting laryngoscope, detachable periscope, and method of endotracheal intubation are disclosed. The device comprises an anterior blade which contacts the tongue and a posterior blade which contacts the hard palate. The blades are moveable apart in a prescribed manner according to the shape of an arm. Manually opening the device causes the airway soft tissue retraction and epiglottic lifting required for visualization of the trachea. The blades remain open via a releasable racheting device. An illuminating periscope can be snapped onto the device allowing indirect tracheal visualization. The entire assembly is sized to fit beneath an airway mask to allow ventilation during the entire intubation process.

33 Claims, 11 Drawing Sheets

PERISCOPE AND RETRACTING LARYNGOSCOPE FOR INTUBATION

FIELD OF THE INVENTION

The present invention relates to surgical instrumentation for the assistance of endotracheal intubation, and more particularly, to a combination of a retracting laryngoscope and a periscope to facilitate the intubation procedure for less experienced intubators.

BACKGROUND OF THE INVENTION

Endotracheal intubation (ETI) is the medical procedure in which a tube is inserted into the trachea of a patient to facilitate breathing or to permit the controlled introduction of gases through the tube. Because the trachea is parallel and anterior to the esophagus, and is normally closed off by the epiglottis, a tube simply introduced orally or nasally will likely travel to the esophagus rather than the trachea. To place the tube through a patient's larynx and into the trachea, it is necessary to displace the epiglottis and other soft tissues which normally obstruct the glottic opening. Additionally, if the patient is not breathing independently, the procedure must be done within approximately 60 seconds to avoid complications due to potentially fatal oxygen deprivation.

Endotracheal intubation can be accomplished by several methods that can be categorized as blind, direct, or endoscopic. Blind methods are those in which the intubator does not see the trachea during the intubation process. These methods include nasotracheal, tactile digital, illuminated stylet, and various doublelumen tube intubations. They are useful when the trachea is hopelessly obscured from view such as during copious bleeding to the larynx. However, blind methods do not offer high success rates, nor do they allow the intubator to confirm the correct placement of the endotracheal tube visually, a serious drawback.

Endoscopic methods make use of a fiberoptic endoscope a miniature lens on the end of a long, thin, fiberoptic bundle. The intubator remotely manipulates the distal end and endotracheal tube into the trachea while viewing through the eye piece at the proximal end. Endoscopic methods are advantageous in that they do allow visual confirmation of proper tube placement. However, they require a significant amount of training and skill, and are expensive, making them financially inaccessible for most ambulance companies and many emergency departments. Hence, endoscopes are not widely used for intubation.

The majority of intubations are performed by direct methods, employing various shaped laryngoscopes, most commonly the Macintosh and Miller blades. Direct methods involve manually retracting the soft tissues and lifting the epiglottis until the trachea can be viewed directly. The endotracheal tube is then manually introduced and proper placement visually confirmed. Direct laryngoscopic intubation (DLI) is the most commonly employed technique in the United States since the equipment needed is affordable and training required moderate.

Direct laryngoscopic intubation is accomplished by performing several steps. Prior to attempting these steps, an oral airway (OA) is commonly inserted into the pharynx to open the airway by lifting the tongue from the posterior pharyngeal wall. Temporizing methods of ventilation are commonly employed such as BVM (bag-valve-mask) ventilation while the intubation equipment is prepared. Briefly the steps of DLI are: 1. stopping ventilation; 2. removing oral airway; 3. opening patient's mouth; 4. differentiating soft tissues; 5. inserting laryngoscope; 6. positioning laryngoscope; 7. retracting via lifting including lifting the epiglottis; 8. visualizing the trachea; 9. inserting endotracheal tube into trachea.

Novice and infrequent intubators commonly experience difficulty with several DLI steps including opening the patient's mouth and inserting the laryngoscope. Inserting an oral airway is a comparatively simple process. The OA is inserted into a minimally opened mouth and slid blindly along the hard palate until the proximal end is seated against the lips, teeth, and other underlying anterior oral structures. The OA is of soft material and thus poses little chance of inflicting trauma such as lacerations or broken teeth. Inserting a laryngoscope, however, is more complex as the mouth must be widely opened; the laryngoscope is made of metal which can more easily cause trauma; and the insertion process cannot be initiated until after the soft tissues have been differentiated correctly.

Insertion of the laryngoscope is further complicated because the trachea is deep and anterior in the pharynx and lies at an approximate 90-degree angle to the oral cavity. Further, in the unconscious patient, the tongue collapses, falling against the posterior pharyngeal wall and the hard palate. The intubator's task is to insert the blade between the tongue and hard palate, advance the tip first posteriorly then inferiorly to the posterior aspect of the tongue, and then advance inferiorly almost to the epiglottis. Being of very soft consistency, the tongue tends to collapse around both sides of the blade and be carried in the direction of the blade's movement. To avoid pushing the tongue further into the throat, the intubator must employ an iterative process of placing the laryngoscope against the tongue, blindly advancing posteriorly, retracting the tongue anteriorly to allow visualization of the current distal tip position, then further blindly advancing. This is continued until the epiglottis can be visualized.

Also, intubators often have difficulty positioning the laryngoscope properly. Improper placement leads to certain failure as epiglottic lifting requires very exact positioning of the distal blade tip to within 0.5–1.0 cm of the target position. However, obtaining the target position for the distal blade tip is difficult because it cannot even be seen until the final movement iteration. Also, there may be blood, vomitus, teeth or other foreign matter obscuring the view; the entire area of focus is rather small, as the tongue tends to collapse around the blade, and thus finding the proper location for the blade tip can be very difficult.

Another difficulty is developing the proper lifting motion. The natural tendency to pivot the laryngoscope like a lever makes success highly unlikely and promotes oral trauma. The proper motion involves a translational movement at approximately 45–60 degrees to the patient's trachea. "Lifting" requires the intubator to apply approximately 20–30 lbs. of force with a fully outstretched arm and to maintain this position for the remainder of the procedure. This must be held steadily, as wavering will cause the pharynx to move with the laryngoscope. It is a physically demanding yet delicate step to hold such an awkward position while applying a steady force. Further, even minimal variance from the required motion, or minimal rotation of the blade will make visualization of the trachea impossible.

Problems also arise when the intubation attempt fails. If the attempt is not completed within approximately 60 seconds (for example: inability to visualize the trachea, improper lifting motion, inability to hold the lifting position long enough to allow tube placement, inability to find the epiglottis amongst the soft tissues, inability to pass the tube into the trachea), it must be aborted. Subsequently, the laryngoscope is withdrawn, the oral airway reinserted, and the patient ventilated for 2–3 minutes (to obtain sufficient systemic oxygenation) before a second attempt can be initiated. The disadvantages of a failed attempt include the 2–3 minute time delay before the second attempt can be initiated, but even more notably, all of the steps successfully performed in the first attempt must be repeated during the second attempt since each attempt begins the process anew.

These commonly encountered problems are inherent in the design of the currently available equipment for DLI, making intubation a heavily skill-dependent process that relies upon the individual intubator's abilities for success.

The prior art shows some attempts at solving the needs of the less experienced intubator. U.S. Pat. No. 5,498,231 to Franicevic discloses an intubating laryngoscope having two blades which pivot about separate axes and a lever to move the ends of the blades apart. Because the device completely blocks the field of view, an optical system and a fiberoptic illumination system are necessary for viewing. The movement of the blades in this device is "beak-like" and inconsistent with movement of the human body. The device is rather complicated and requires many elements which would be too expensive for inclusion on many emergency vehicles.

U.S. Pat. No. 5,178,132 to Mahefky discloses a laryngoscope which employs the chin of a patient as a reference fulcrum for enabling controlled pivotal movement of a laryngeal blade. While this device is designed to prevent injury, it does not assist the intubator in maintaining the mouth in an open position, nor does it provide a means for viewing the airway.

U.S. Pat. No. 4,793,327 to Frankel discloses a mouth-holding device having a lower and an upper arm. An esophageal guide passes through a bracket which is attached to the upper arm. The lower arm includes notches adapted to receive a catch of the upper arm. An adapter on the guide allows for the insertion of an endotracheal tube having an adapter sized to mate with the guide's adapter. While the guide allows for blind insertion, the device does not press the tissue within a patient's mouth in a manner which opens the airway, does not provide for visualization within the patient's mouth, and requires specially designed endotracheal tubes which may not be readily available.

Thus, there is a need for a device which can assist an intubator in easily and quickly accomplishing direct laryngoscopic intubation. There is further a need for such a device which is inexpensive enough to be financially accessible for any emergency vehicle. There is further a need for such a device which enables indirect visualization of a patient's airway. There is further a need for such a device which performs the skill-required steps of the intubation process. There is further a need for a device which provides hands-free, stable retraction for insertion of the endotracheal tube. There is further a need that such a device fit entirely beneath a standard airway mask in order that intubation can always be achieved in a single attempt.

SUMMARY OF THE INVENTION

Thus, it is an object of the present invention to provide a retracting laryngoscope which displaces the patient's oral and pharyngeal tissues to open and maintain open, the patient's airway such that tracheal visualization can be enacted.

It is another object of the present invention to provide a periscope which interacts with the retracting laryngoscope to offer an indirect view of the patient's airway.

Other objects will in part be obvious and in part appear hereinafter.

The disclosed design incorporates a tissue retractor, a periscope, and a method of use that eliminates the above-stated problems inherent in the currently available intubation equipment. These advantages over the prior art are significant and are enabled only by the disclosed design.

First, the disclosed device allows for an easy and quick performance of step 3 (opening the patient's mouth), steps 5 and 6 (inserting and positioning the laryngoscope), and eliminates entirely the need for step 4 (differentiating the soft tissues). The mouth need not be opened widely and the intubator need only slide the disclosed device blindly along the hard palate to find the proper position, rather than search through the soft tissue to locate the correct path to the base of the tongue. The action is similar to the proper insertion of an oral airway. In addition, the present invention is an advancement over the prior art in that complete insertion into the mouth automatically places the distal tip of the laryngoscope at the required target position. Thus in the present invention, steps 5 and 6 (inserting and positioning the laryngoscope) are easily (and quickly) performed at the same time, in under 5 seconds. Since the distal blade tip is properly and accurately positioned, the intubator need not possess the skill required, nor use time to find the airway and epiglottis amongst the collapsed tissue, thus eliminating the fourth step, differentiating the soft tissues. Finally, in the closed position, the laryngoscope can perform the function of an oral airway.

Second, no prior art device performs the actual lifting motion required of DLI. All others rely upon the intubator to do this. The lift itself requires an exacting and physically demanding motion that is not easily learned, and is often misperformed, thus causing failed attempts. In contrast, when the blades of the present invention are moved apart, the anterior blade retracts the airway soft tissues, and lifts the epiglottis in the required motion. This motion is predetermined by the shape of the connecting arm. Thus the device performs the retracting and lifting motion automatically, alleviating the need for the intubator to be skilled or experienced in the performance of this step. In addition, the disclosed device maintains the soft tissue retraction and epiglottic lifting with a locking ratchet mechanism. This affords "hands-free", stable tissue retraction whereas the prior art laryngoscopes require that one hand maintain the physically intensive lifting motion while the remainder of the intubation steps are performed.

Third, the disclosed device is small enough to fit wholly under a standard airway mask, thus not interfering with either proper air mask placement or BVM ventilation, a significant advancement over the prior art. In the prior art, should ventilation be needed, the intubation attempt must be terminated and the laryngoscope removed as the laryngoscope and BVM mask cannot occupy the mouth area at the same time. Subsequent intubation attempts have to be reinitiated at step one. With the disclosed device, should ventilation be needed, the intubation attempt is merely suspended. Whether in the closed, open, or periscope-applied arrangement, the BVM can simply be reapplied to the patient's face (over the top of the device) and ventilation applied. When the patient is sufficiently oxygenated the BVM mask is removed, and the intubation process resumed at the point suspended. Only a single attempt is ever needed, thus reducing the time of the intubation process and significantly reducing risk to the patient.

Fourth, although the non-endoscopic prior art describes optical laryngoscopes having devices (prisms, mirrors) for viewing pharyngeal structures, none incorporates the optics as a piece separate from the laryngoscope, and that snaps into proper position. Unique advantages in method result from this design. Currently, if the optics become fogged or obscured, the entire optical laryngoscope must be removed and the intubation attempt aborted, necessitating the several minutes delay while the patient is ventilated and the intubation process restarted from the beginning. However, with the disclosed device, the positioning of the retractor is maintained should the optics portion need to be removed, allowing the intubator to clean the lens, snap it back into proper position, and resume the intubation process in only a few seconds. Further, the optics are not inserted into the mouth until after the retractor is ratcheted open, reducing the chances of their becoming soiled and allowing for suctioning to remove blood, etc.

Another advantage of the disclosed device over the prior art is that the optical device allows the trachea to be viewed from the posterior aspect of the pharynx, providing a much more advantageous view and only possible with an optical device that is independent of the retraction device. Because the trachea lies at an approximate 90-degree angle to the oral cavity, its direct, line-of-sight view is obstructed by the inside or anterior corner of the 90-degree angle. Viewing is accomplished either by pushing the inside corner anteriorly (anterior tongue retraction) to achieve a straight line of sight or by viewing around this corner via a periscope from a posterior position (i.e., positioned near the outside corner). When the optical assembly forms a single unit with the laryngoscope, the position of the optics is dictated by the position of the laryngoscope, rather than by optimal viewing position. Further, the anterior position of the optics tends to obstruct the "line-of-sight" tracheal view. In contrast, the present invention includes a separate optical assembly whose position can be adjusted independently from the laryngoscope and then snapped into a stable position. Having a separate optical system allows it to be placed at the more advantageous posterior position and adjusted to the specific conditions of the individual patient. This is particularly advantageous in cases where the trachea is anatomically so anterior that no amount of anterior tongue retraction allows direct visualization as well as when the neck cannot be manipulated to decrease the oral-tracheal angle (such as the spinally immobilized patient) prior to attempted visualization.

Fifth, the disclosed laryngoscope can perform the functions of an oral airway as the prior art cannot. When in position with the ratchet closed, and seated against the lips and underlying anterior structures, the front blade maintains airway patency, lifting the tongue off of the posterior pharynx.

The automatic positioning and retracting laryngoscope enables a simple and quick method of intubation. It automatically performs the laryngoscopic positioning and retracting steps of intubation. Endotracheal intubation is always performed in "one attempt", a crucial advantage since during intubation "each second counts". The present invention allows the intubator both hands free to perform other functions, while having more stable tissue retraction.

The present invention is designed to assist in the placement of air tubes, and is specifically designed for use by inexperienced paramedics, although experienced physicians may take advantage of the invention's benefits as well. Because the device can be made inexpensively, most emergency companies should be able to afford it. The invention preferably consists of two parts: an illuminating periscope and a retracting laryngoscope. The retracting laryngoscope preferably combines a curved blade (similar to that of a laryngoscope) for engaging the soft tissues, a straight blade engaging the hard palate, and an arm for moving the blades apart to open the mouth and lift the soft tissues in the proper direction.

Preferably, the arm is in the middle of the retractor. This way, the periscope can be placed on one side of the arm while the tube is being inserted on the other side of the arm. Alternatively, the arm may be on the side of the retractor. Also, the arm is preferably provided with a radius of curvature of about 3.5 inches for accomplishing the movement of the opening of the mouth, although the arm may be straight and angled relative to the two blades.

A procedure for simply and inexpensively accomplishing intubation is envisioned. The retracting laryngoscope is placed into the patient's mouth with the curved blade facing anteriorly. It is slid blindly along the hard palate until seated against the lips and underlying anterior structures. Then, the retractor is opened. As the blades separate, the arm requires the blades to move with a motion which presses the patient's soft tissues, and lifts the epiglottis, making the airway visible. The retracting laryngoscope remains open with the ratchet. Then, the periscope can be inserted into the mouth and snapped into place onto the retractor for a clear, stable view of the airway. Then, the endotracheal tube can be inserted.

The foregoing and other features and advantages of the invention will be more readily understood and fully appreciated from the following detailed description, taken in conjunction with the accompanying drawings.

DETAILED DESCRIPTION OF THE PREFERRED EMBODIMENTS.

Figure 1:
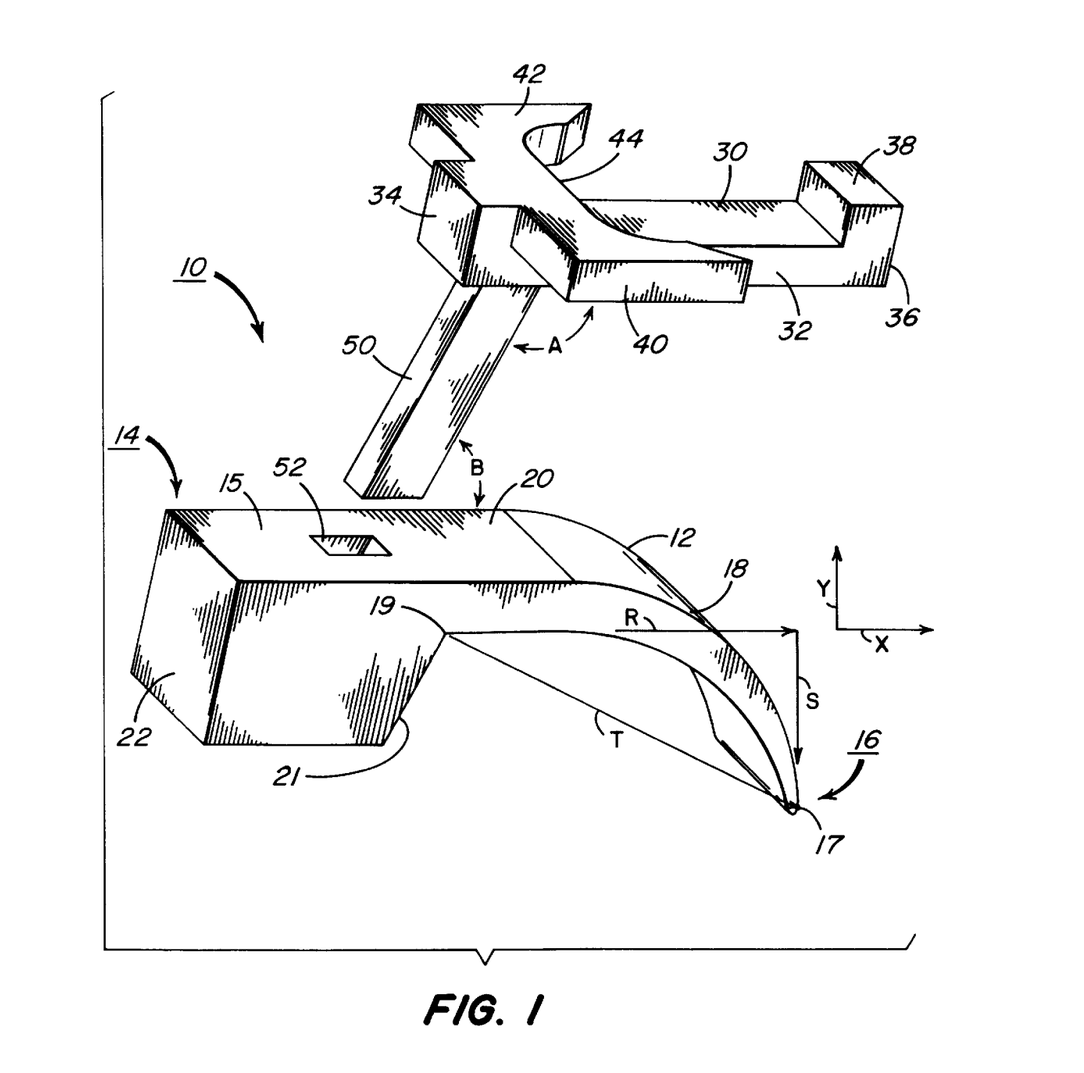
FIG. 1 shows a side perspective view of one embodiment of a retracting laryngoscope with the blades apart.

FIG. 1 shows a retracting laryngoscope 10 according to a first embodiment of the present invention. The laryngoscope 10 includes a first blade 12 (a "tongue" blade) having a proximal end 14 and a distal end 16. The blade 12 is essentially a curved blade, with a curved section 18, although the blade 12 may also include a straighter section 20 towards the proximal end 14 of the blade 12. The shape of the curved blade 12 is designed to retract the tongue and soft tissues of a patient's mouth, as would a conventional laryngoscope. The proximal end 14 may also include an arm receiving section 22, for receiving an arm as will be discussed below. In addition, the arm receiving section 22 includes, on its distal facing side, a patient-abutting surface 21. The surface 21 is designed to press against the patient's lower lip, teeth, and other underlying external oral structures. When the laryngoscope 10 is fully inserted into a patient's mouth, such that the surface 21 presses against the patient as discussed above, the distal point 17 of the blade 12 will automatically be correctly positioned into the vallecula (anatomic area of the patient's pharynx where the epiglottis intersects the tongue at an approximately 20–30 degree angle) for lifting of the epiglottic tissue and retracting of other soft tissue required for tracheal visualization. This correct positioning into the vallecula can only be achieved through the vector relationship between the corner point 19 (the corner defined by the intersection of the blade 12 and the surface 21) and the distal point 17. While the dimensions and curvature of sections 18 and 20 may be changed, the vector relationship between points 17 and 19 is essential for automatic correct positioning. The relationship is defined by vectors R and S as shown in FIG. 1, with vector R being parallel to surface 15, and vector S being perpendicular to vector R and pointing in the negative direction, as defined by the X-Y axis legend. The inventor has found that if point 19 defines point (0,0), then point 17 should lie approximately on point (6.5,–3). In other words, for an average adult, vector R would be about 6.5 cm and vector S would be about 3 cm, with the distance between points 19 and 17, as defined by vector T, being approximately 7.2 cm. Of course, the dimensions would change for much larger adults and for small children, but the vector relationship would retain the same ratio, that is, point 17 would be at point (6.5Q,–3Q) where Q is 1 for an average adult, less than 1 for a child or smaller adult, and greater than 1 for a larger adult. An average adult may be defined as being approximately 150 pounds and about 5 feet 8 inches tall. As with standard laryngoscopes, it may be desirable to have five or six different sizes available for adults.

The laryngoscope 10 further includes a second blade 30 which is essentially a straight blade, with a straight section 32. The blade 30 has a proximal end 34 and a distal end 36. The distal end 36 may be provided with a distal block 38 which extends above the surface of the blade 30. The distal block 38 is adapted to abut the roof of a patient's mouth. The proximal end 34 of the blade 30 may further include a transverse member 40 which may be essentially planar and adapted to abut the patient near the upper lip and teeth. An inner side 44 may be essentially U-shaped for forming an anatomically conforming area. In addition, the shape of the inner side 44 provides the laryngoscope with rotational stability. That is, the laryngoscope is prevented from rotating within the patient's mouth when the laryngoscope is firmly seated against the patient's lips and underlying anterior tissues. It is also within the scope of this invention to provide a transverse member 40 which just uses one side, e.g. the left side or the right side of the proximal end 34, as that would still provide rotational stability to the inserted laryngoscope. The upper surface 42 and/or inner surface 44 of the transverse member 40 may also include a soft padded layer for preventing abrasion to the patient's teeth and upper soft tissue.

Although first blade 12 has been described as a curved blade, it is within the scope of this invention to use a straight blade or even a blade with a directionally controllable distal portion. Thus, any shape or configuration of a tongue blade could be used including, but not limited to, hinged, adjustable, straight, curved, channeled, side-flanged, various sized and other anatomically conforming shapes, etc. In addition, the blade 12 could be provided with ports usable for suction or oxygenation (e.g. to blow oxygen to the blade tip during an intubation process). The blade 12 could further include integral ports for endoscope adaptation or instrument use. A guide could extend from the surface of the blade 12 for guiding an endotracheal tube or even an endoscope or tool. Such ports and guides could also be provided within and/or on the blade 30, as applicable. Likewise, it is within the scope of this invention to form blade 30 into other shapes, such as more anatomically conforming designs, or any of the other shapes described above with respect to the first blade 12.

Figure 2:
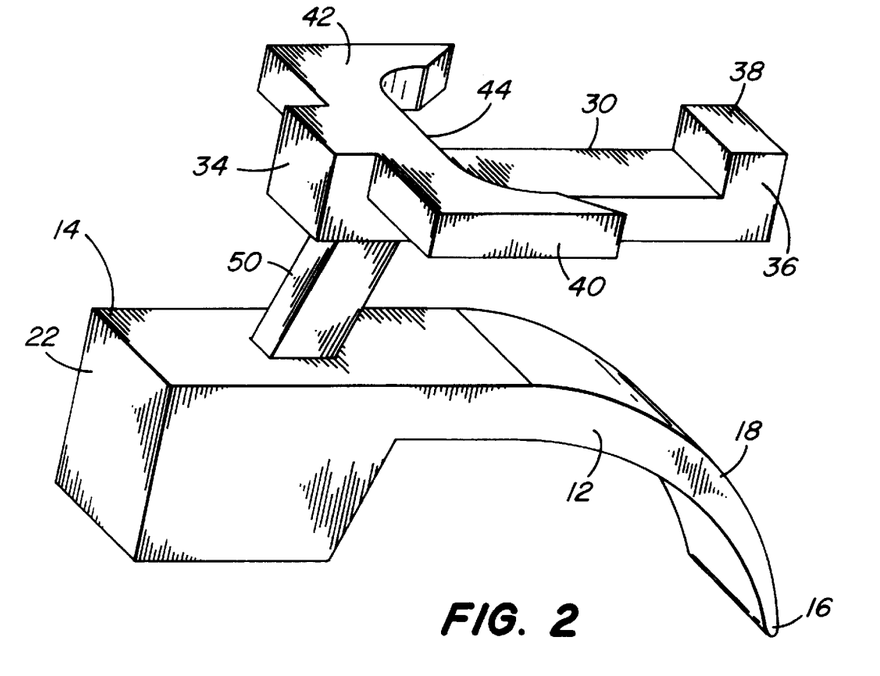
FIG. 2 shows a side perspective view of the retracting laryngoscope of FIG. 1 with the blades in an open position.
Figure 3:
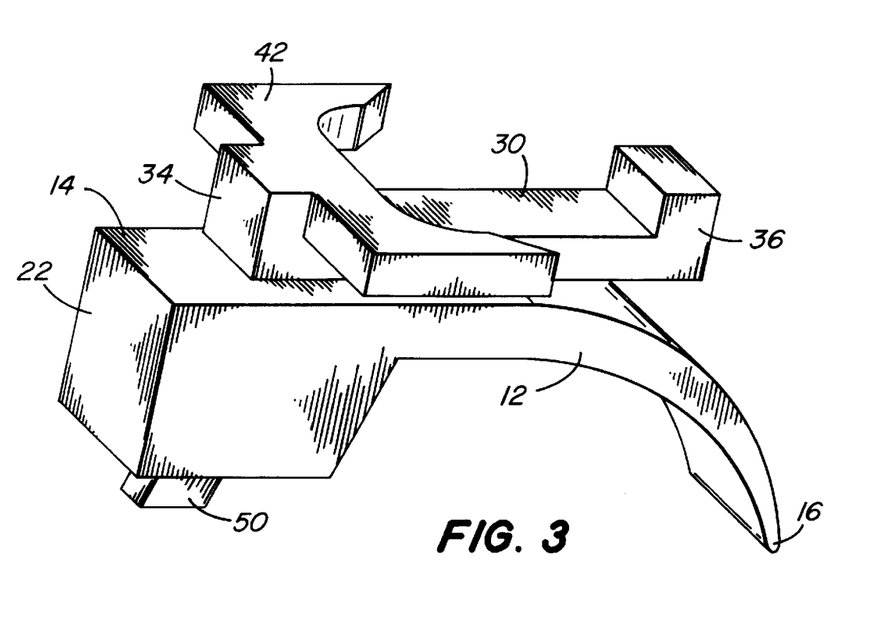
FIG. 3 shows a side perspective view of the retracting laryngoscope of FIG. 1 with the blades in a closed position.

The two blades 12 and 30 are movable relative to one another through arm 50. The arm 50 shown in FIG. 1 is essentially straight and is rigidly connected to the blade 30 at an angle A, which is preferably between the range of 130 degrees to 160 degrees, and is preferably about 145 degrees. The arm receiving section 22 includes an angled opening 52 which is substantially the same size as, but slightly larger than the arm 50, to allow a smooth entry of the arm 50 into the opening 52, as shown in FIG. 2. The opening 52 is angled such that the arm 50 defines an angle B to the first blade 12 which is preferably between the range of 20 degrees to 50 degrees, and is preferably about 35 degrees. The angle B is also preferably 180 degrees minus the angle A so that the blade 30 and the blade 12 move apart from one another along a skewed axis defined by the arm 50. As shown in FIG. 3, the opening 52 preferably extends through the entire arm receiving section 22 to allow passage of the arm 50 from a back side to a front side of the section 22. In this closed position, the straight blade 30 abuts the straight section 20 of the curved blade 12. The retracting laryngoscope 10 may be easily inserted into a patient's mouth in this closed position, and then moved to an open position as shown in FIG. 2. As the retracting laryngoscope 10 is moved from the closed position to the open position, the angle of the arm 50 relative to the blades 12 and 30 moves the blade 12 to retract the tongue and other soft tissues as well as to lift the epiglottis to enact airway opening.

Figure 4:
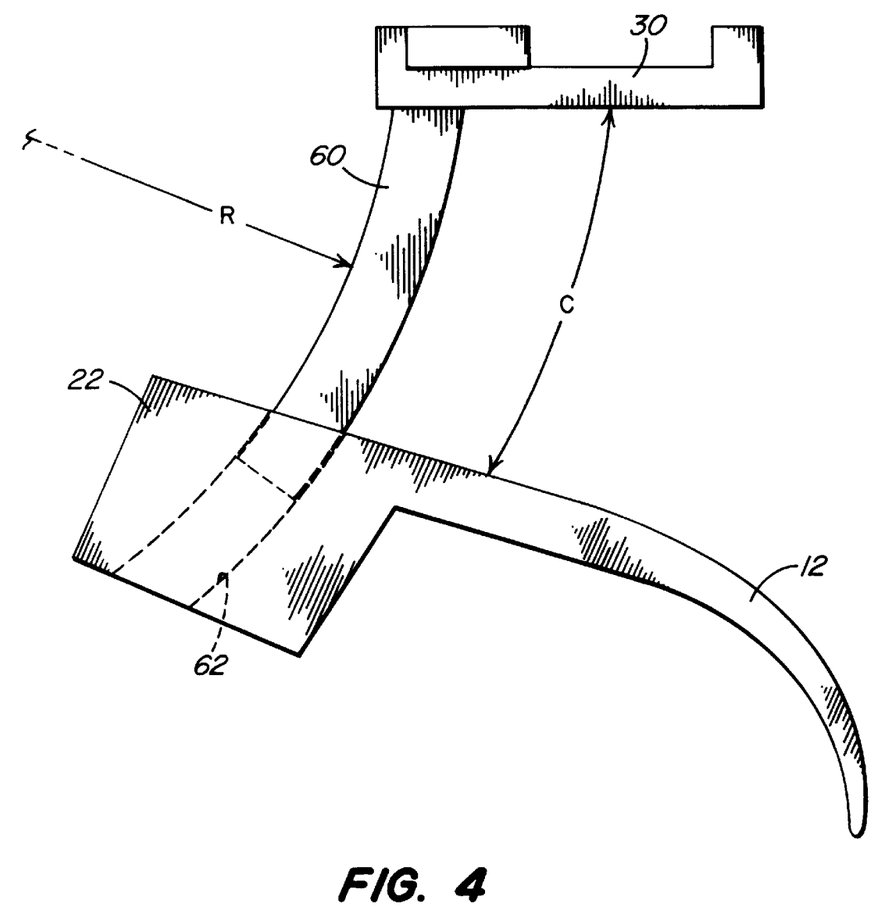
FIG. 4 shows a side view of a retracting laryngoscope having a curved arm and in the open position.

Turning now to FIG. 4, the same retracting laryngoscope 10 is shown with the exception of the arm 60 which is provided with a radius of curvature between 3 to 4 inches, and is preferably about 3.5 inches. That is, the curvature of the arm 60 defines an arc which could lie on a circle having a radius of 3.5 inches. The arm receiving section 22 includes a correspondingly shaped curved opening 62 for receiving the arm 60. Otherwise, the components of the retracting laryngoscope 10 remain the same in this embodiment, that is, the straight blade 30 and the curved blade 12 may be unchanged. When in a closed position, not shown, the straight blade 30 and the curved blade 12 may abut as in the previous embodiment. However, when the blades 30 and 12 are separated, they follow the path defined by the curved arm 60 which changes the angle C between the blades 12 and 30. When the angle is approximately between 30 and 40 degrees, and preferably about 35 degrees, the retracting laryngoscope has automatically opened the airway of the patient for insertion of an endotracheal tube, by correctly angling the curved blade 12 against the patient's tongue and enacting epiglottic lifting.

Although both arms 50 and 60 are shown with a rectangular cross-section, it should be understood that any cross-section is within the scope of this invention. For example, the end effect of the blade movement would remain the same if the arm had a circular or a triangular cross-section. Thus, any other shape of an arm which determines blade movement is within the scope of this invention.

Figure 5A:
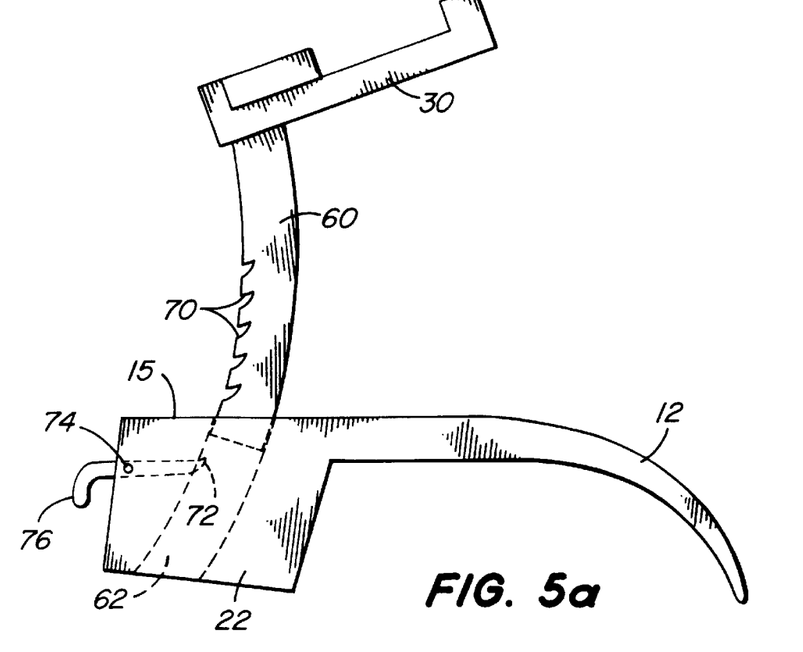
FIGS. 5a–5c show a side view of one embodiment of a locking mechanism for the retracting laryngoscope of the present invention.
Figure 5B:
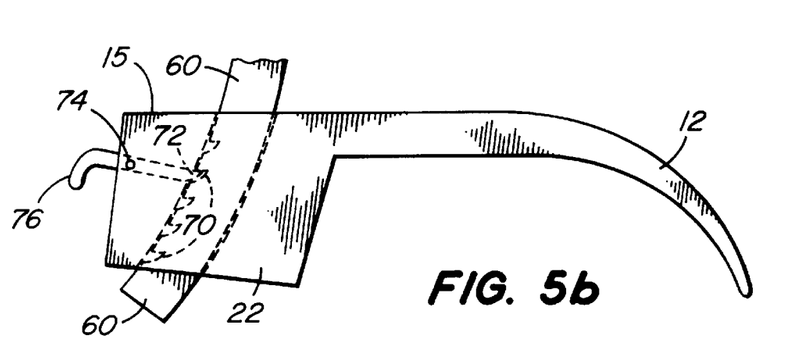
Figure 5C:
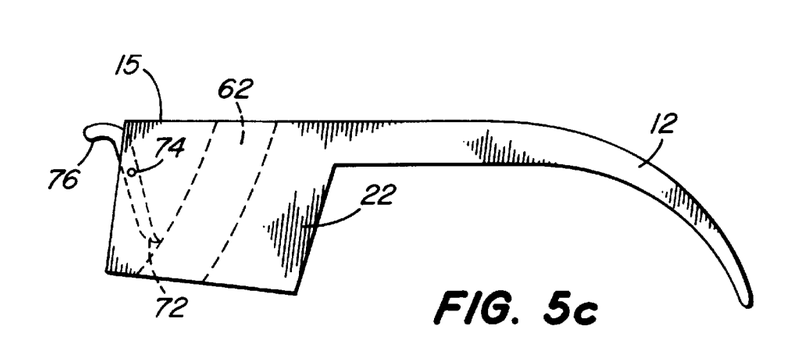

When the retracting laryngoscope is opened, it automatically manipulates the patient's soft tissues to allow insertion of the endotracheal tube. Once opened, the retracting laryngoscope is preferably lockable in place. FIGS. 5a–5c show one embodiment of a locking mechanism which includes teeth 70 on the arm 60 and a latching pawl 72 within the opening 62 in the arm receiving section 22 for engagement with one of the teeth 70. The latching pawl 72 is biased in the position shown in FIG. 5a. When the arm 60 is within the opening 62, as in an initial closed position, the latching pawl 72 is engaged with a tooth 70 on the arm 60. The blades 12 and 30 may be separated from each other with little effort, as the latching pawl 72 pivots about the axis defined by the spring 74 and clicks past each tooth 70. Because the pawl 72 is curved upwardly and biased by the spring 74 in the position shown in FIG. 5a, and the teeth 70 are opened downwardly, the pawl 72 securely holds the retracting laryngoscope 10 in an open position. When it is desired to close the laryngoscope, a release mechanism 76 may be pushed upwardly as shown in FIG. 5c, with a force greater than the biasing force, to move the pawl 72 out of the way of the opening 62 to allow the arm 60 to be pushed downwardly.

Alternatively, the teeth 70 could be positioned on a side of the arm 60 and a catch located on upper face 15 pointing inwardly towards opening 52 in arm receiving section 22. With the arm pushed up against an opposite side of the opening 52 and the teeth 70 slanted backwards on a side surface of the arm, the arm may slide freely within the opening 52 such as during the blade-opening movement, with the teeth 70 sliding over the catch. Once opened to position, the arm may be shifted against the catch, locking the arm teeth 70 against it. The intrinsic forces of the patient's jaws tend to close the mouth, thus retaining the teeth against the catch. Closure of the instrument is accomplished by moving the arm away from the catch to disengage the teeth, allowing the arm to move freely within the opening 52.

Figure 6A:
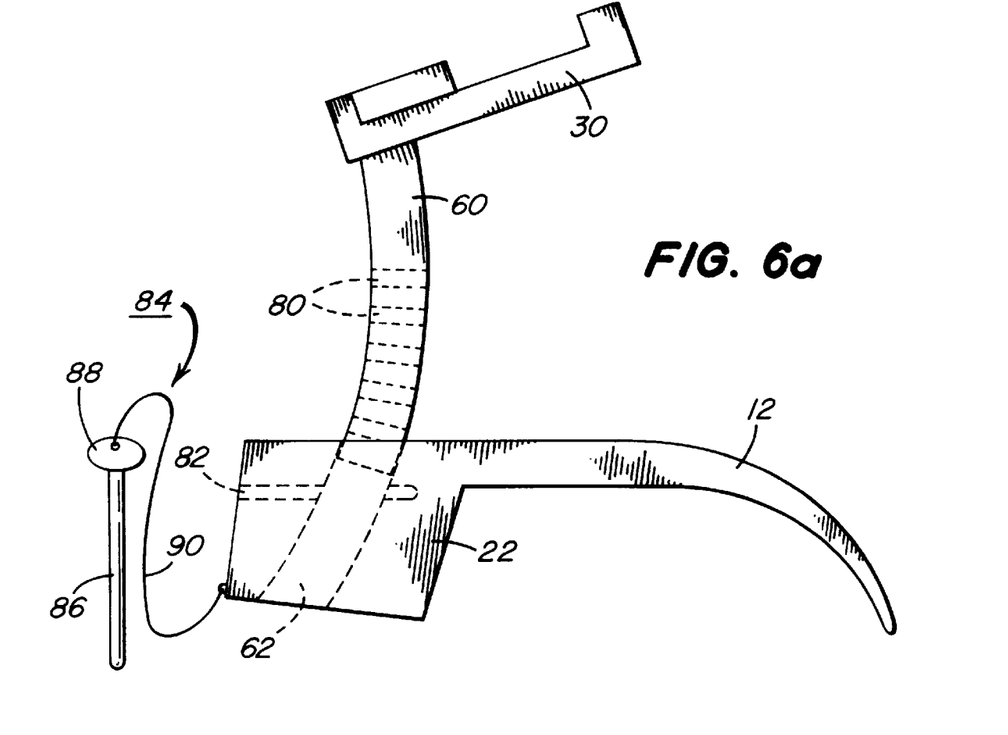
FIGS. 6a–6b show a side view of another embodiment of a locking mechanism for the retracting laryngoscope of the present invention.
Figure 6B:
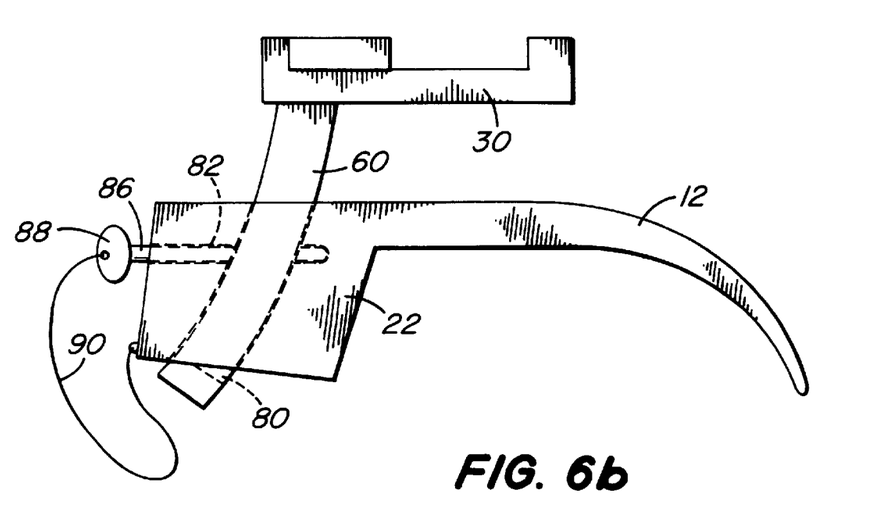

Another embodiment of a locking mechanism is shown in FIGS. 6a–6b. A series of holes 80 may be drilled or molded into the arm 60 and a hole 82 of substantially corresponding size provided in arm receiving section 22. A pin 84 with stem 86 and head 88 may be attached by tether 90 to the section 22. When a desired separation between the blades 12 and 30 are reached as shown in FIG. 6b, the pin 84 may be inserted into the hole 82 and aligned hole 80 to secure the retracting laryngoscope in place.

Although two specific embodiments of locking mechanisms are shown in FIGS. 5 and 6, other locking mechanisms are within the scope of this invention, including, but not limited to, thumbscrews, pins, teeth, etc. Also, the locking mechanisms shown are usable on the straight arm 50. In addition, although the locking mechanisms are shown with respect to the curved blade 12, it is also within the scope of this invention to rigidly connect the arm 50 or 60 to the curved blade 12 and have it pass through an opening in a proximal end 34 of the straight blade 30. Thus, the locking pawl 72 or the pin 84 could be provided in the proximal end 34 of the blade 30.

Figure 8:
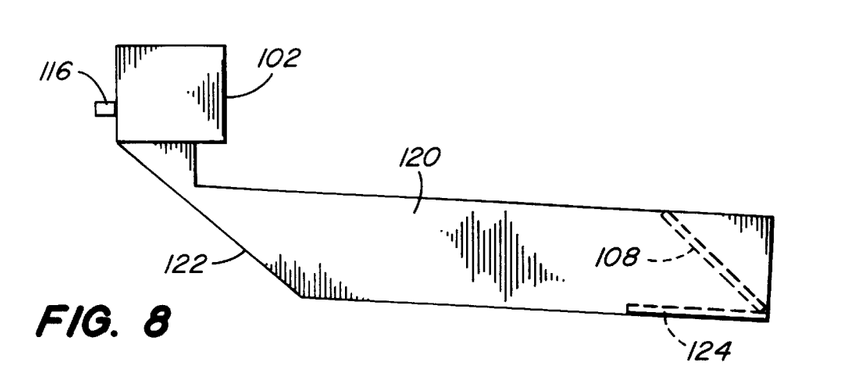
FIG. 8 shows a side view of another embodiment of a periscope for use with the retracting laryngoscope of the present invention.
Figure 9:
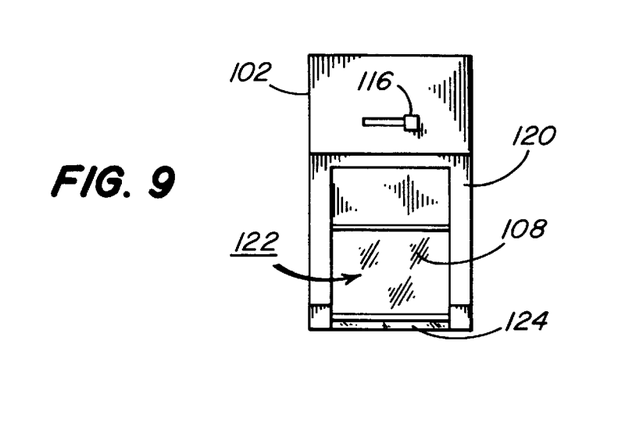
FIG. 9 shows a top view of the periscope of FIG. 8.
Figure 10:
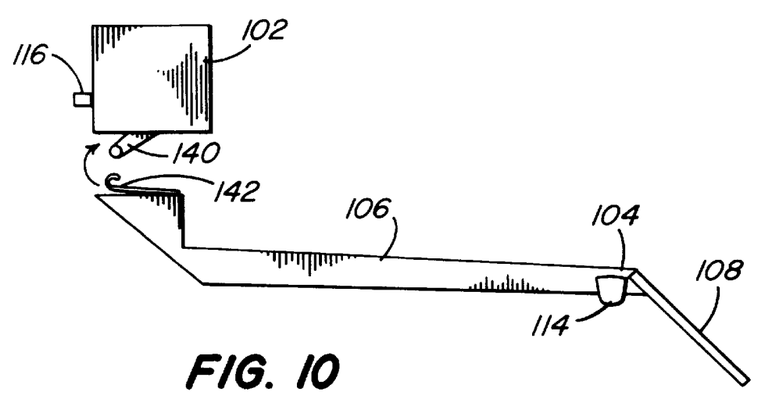
FIG. 10 shows a side view of the periscope of FIG. 7 having a detachable portion.

Turning now to FIGS. 7–13, a periscope for use with the retracting laryngoscope of the present invention is shown. Once the retracting laryngoscope 10 has been put in place in the patient's mouth, it can be rapidly opened and locked into position, making the airway of the patient accessible. Using the periscope of the present invention, an endotracheal tube can be inserted under a clear view of the airway. The periscope 100 shown in FIG. 7 includes a distal end 104 and a proximal end 102. Connecting the distal end 104 to the proximal end 102 is an elongated body 106 which is preferably about 3 inches long. Attached to the distal end 104 is an angled mirror 108. The intubator 112 is thus provided with a view along path 110. The present invention allows for proximal viewing of the trachea by the insertion of the periscope in a posterior aspect of the patient's pharynx. To further assist in this view, a light source 114, such as a light bulb, may be attached to the distal end 104 of the periscope 100 next to the angled mirror 108. The batteries (not shown) for powering the light source 114 may be contained in the proximal end 102, which also houses the switch 116 for turning the light source 114 on or off via wires 118. Alternatively, the light source could be externally powered in which case an electrical cord could extend from the proximal end 102. Although shown on the exterior of the periscope 100, it is apparent that the periscope 100 could be designed to contain the wires 118 and light source 114. Also, it is within the scope of the present invention to provide the light source 114 in the proximal end 102 with illuminating optical fibers that carry the light from the light source 114 to the distal end 104. Further, as shown in FIG. 10, the proximal portion 102 could be separable from the elongated body 106. Thus, it may be possible to form the body 106 and the distal portion 104 from inexpensive, disposable materials while the proximal portion 102 is made from a reusable, sterilizable material. The proximal portion 102 may snap onto the proximal end of the elongated body 106 using a connector 140 which mates with a latch 142 on the body 106. Of course, any other suitable connection mechanism is within the scope of this invention.

Figure 7:
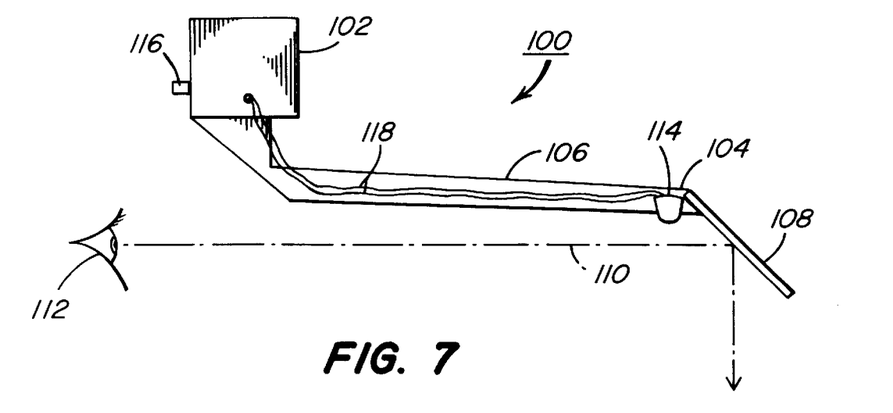
FIG. 7 shows a side view of one embodiment of a periscope for use with the retracting laryngoscope of the present invention.
Figure 11:
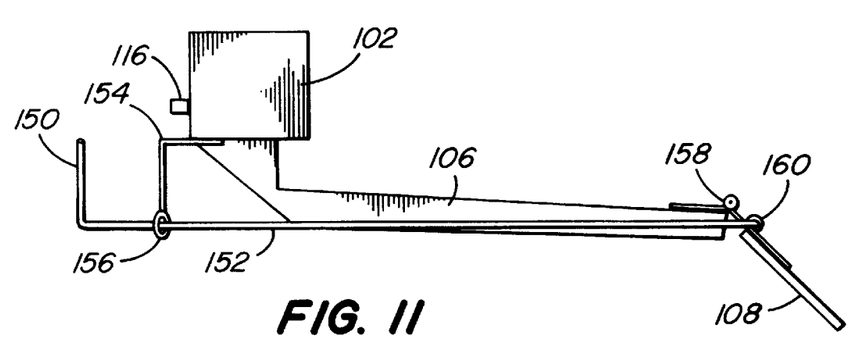
FIG. 11 shows a side view of a periscope having a controllable mirror at the distal end.
Figure 12:
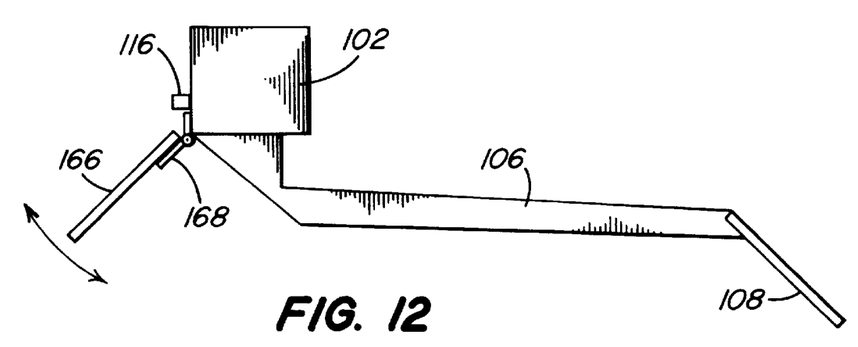
FIG. 12 shows a side view of a periscope having a movable lens at the proximal end.
Figure 13:
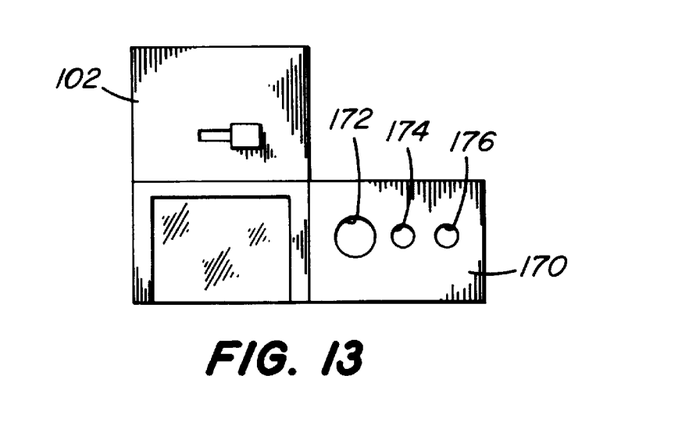
FIG. 13 shows a top view of a periscope provided with auxiliary ports.
Figure 14:
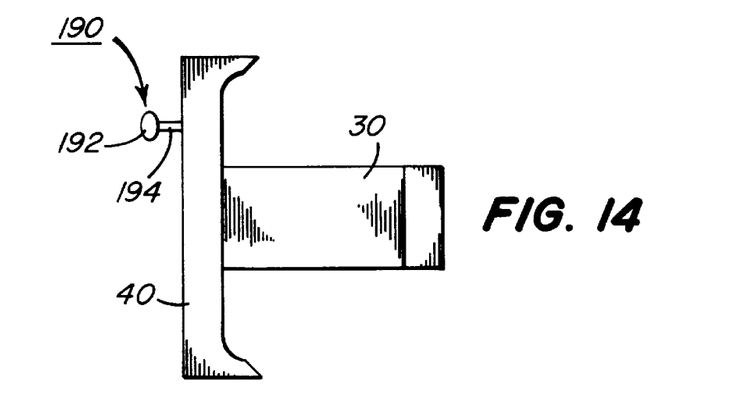
FIG. 14 shows a front plan view of an upper blade having a snap-on projection.
Figure 15:
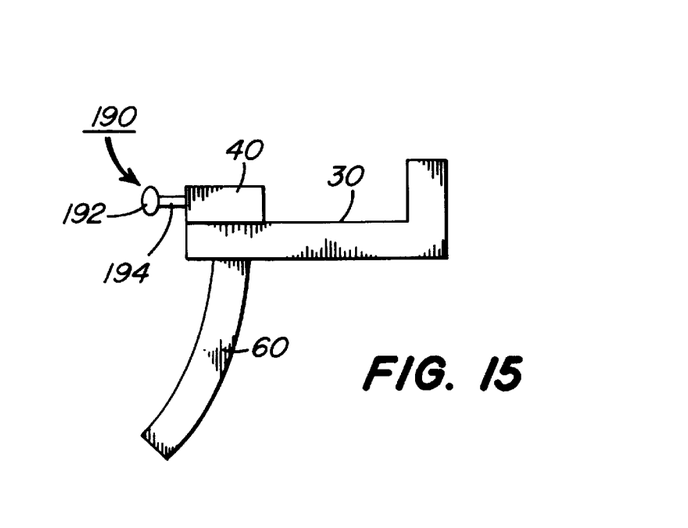
FIG. 15 shows a side plan view of the upper blade of FIG. 14.
Figure 16:
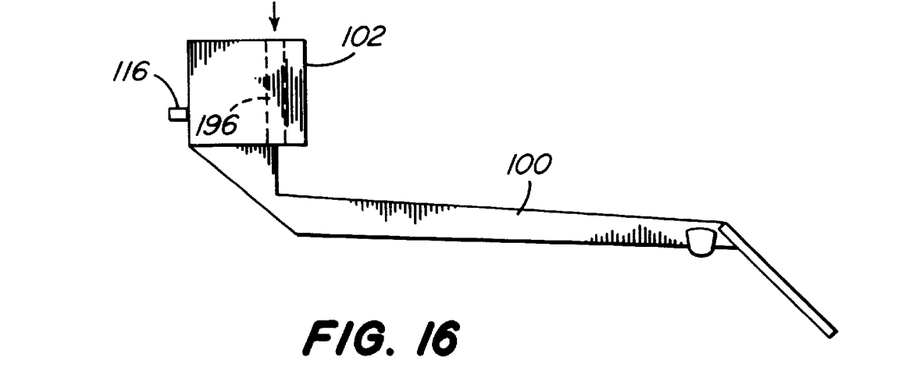
FIG. 16 shows a side plan view of a periscope with aperture for accepting the snap-on projection of the upper blade of FIG. 14.
Figure 17:
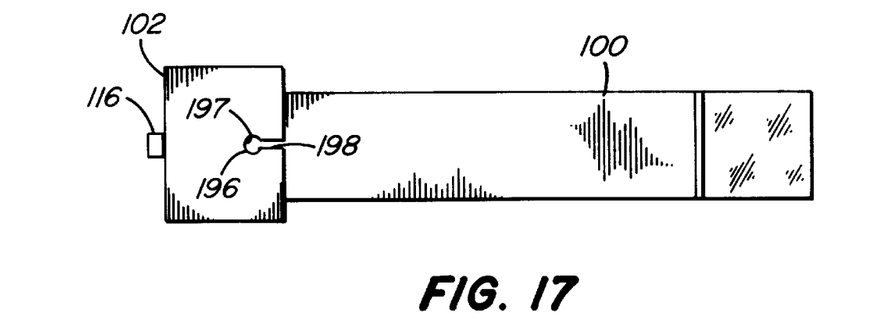
FIG. 17 shows a front plan view of the periscope of FIG. 16.

The embodiment shown in FIG. 7 uses an angled mirror 108 which is "open" to the surrounding environment. As shown in FIGS. 8 and 9, the periscope may include an elongated body which forms what is essentially a tunnel 120 to the mirror 108. The tunnel 120 may include an opened proximal end 122 and a transparent window 124 at the distal end. In either embodiment of the periscope, the angled mirror 108 could be made controllable. That is, the mirror 108 could be connected to a rotatable knob or other control member at the proximal end 102 such that the angle or direction of the mirror can be remotely altered, to customize the view for each patient, without having to move the entire periscope. For example, FIG. 11 shows the mirror 108 hinged by hinge 158 to elongated body 106 and controllably movable by a control arm 150 located proximally of the proximal end 102. The control arm 150 is attached to a connecting member 152 which extends the length of the body 106 and attaches to the mirror 108 via a movable connector 160. The connecting member 152 may be further guided by guide loop 156 attached to support 154 connected to proximal end 102. Thus, the angle and direction of the mirror 108 may be changed under influence of the control arm 150. Alternate methods of controlling movement of the mirror 108 are also possible, although it is preferred that the cost of such control features be kept to a minimum. For example, the mirror 108 could have multiple settings, such as by a friction mount or ratcheting hinge, and the mirror 108 could be manually moved to a selected setting prior to insertion of the periscope into the mouth. Although the mirror 108 is shown as planar, various kinds of mirrors are within the scope of this invention, such as, but not limited to, convex, concave, fresnel, etc. In addition, the periscope of the present invention could include an additional lens or other optics, prisms, etc. proximal to the mirror to magnify the view seen along path 110. For example, FIG. 12 shows a hinged magnifying lens 166 connected to the proximal portion 102 via hinge 168. The hinge 168 could be a friction hinge such that movement of the mirror 166 in one direction or the other retains it in the selected location until it is physically moved again. Furthermore, as discussed with respect to the blades 12 and 30, the periscope could also include auxiliary ports for providing access for endotracheal tube insertion, suction, and oxygen. As shown in FIG. 13, a section 170 could extend from the periscope and provide ports 172, 174, and 176 for endotracheal tube insertion, suction, and oxygen, respectively. Of course, the arrangement and function of these ports could be varied.

Preferably, when the periscope 100 is positioned between the blades of the laryngoscope, it is securely yet detachably attached thereto, such as by a snap-on connection. As shown in FIGS. 14–17, The connection may consist of a projection 190 extending from the transverse member 40 of the upper blade 30 which fits snugly into a correspondingly shaped aperture 196 in the proximal portion 102 of the periscope 100. The projection 190 may comprise an enlarged head 192 and a smaller neck 194 which connects the head 192 to the member 40. Likewise, the aperture 196 may comprise an enlarged portion 197 and a thinner portion 198. The thinner portion 198 opens up to the distalmost side of the proximal portion 102. In use, the periscope 100 can be placed between the blade 30 and the blade 12 and directly adjacent the blade 30 with the proximal portion 102 generally aligned adjacent the projection 190. Then, the periscope 100 can be pushed towards the projection 190 until the projection 190 is seated securely within the aperture 196. In practice, the patient would most likely be in a supine position, and therefore the periscope 100 would be pushed horizontally over the projection 190, and thus would be at no risk of becoming displaced due to gravity. Although one particular connection is described with respect to FIGS. 14–17, other alternative snap-on connections as well as other secure yet detachable connections are within the scope of this invention.

Figure 18:
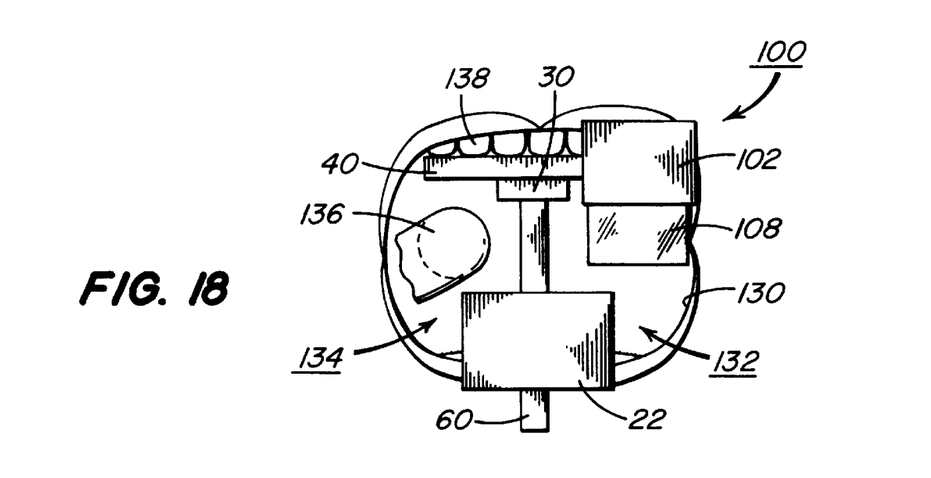
FIG. 18 shows a top view of the retracting laryngoscope, periscope, and endotracheal tube of the present invention positioned in a patient's open mouth.

As shown in FIGS. 1–3, the arm 50 connects a central section of the proximal end 34 of the blade 30 to a central section of the proximal end 14 of the blade 12. A similar connection could be provided with arm 60. The retracting laryngoscope may be inserted into the patient's mouth 130 and opened as shown in FIG. 18 with the transverse member 40 abutting the patient's teeth 138. The periscope 100 can then be inserted into the mouth opening 130 and snapped, detachably, into place onto transverse member 40. The central connection of the arm 50 or 60 allows the mouth opening 130 of a patient to be essentially divided into two "working areas". A first working area 132 can be used to insert the periscope 100 to gain a clear view of the patient's airway using mirror 108. A second working area 134 can be used to insert the endotracheal tube 136. Because the periscope 100 is secured in place, the intubator's hands are freed from having to hold it throughout the remainder of the intubation process. The proximal end 102 of the periscope 100 will not press against, fall into, or otherwise interfere with the endotracheal tube 136 because it is separated from the endotracheal tube 136 by the arm 50 or 60.

Figure 19:
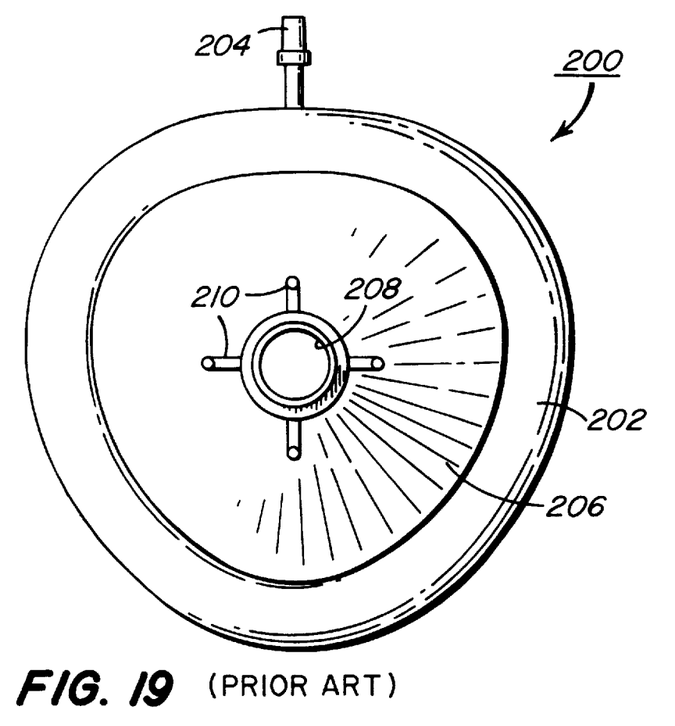
FIG. 19 shows a top view of a prior art airway mask.
Figure 20:
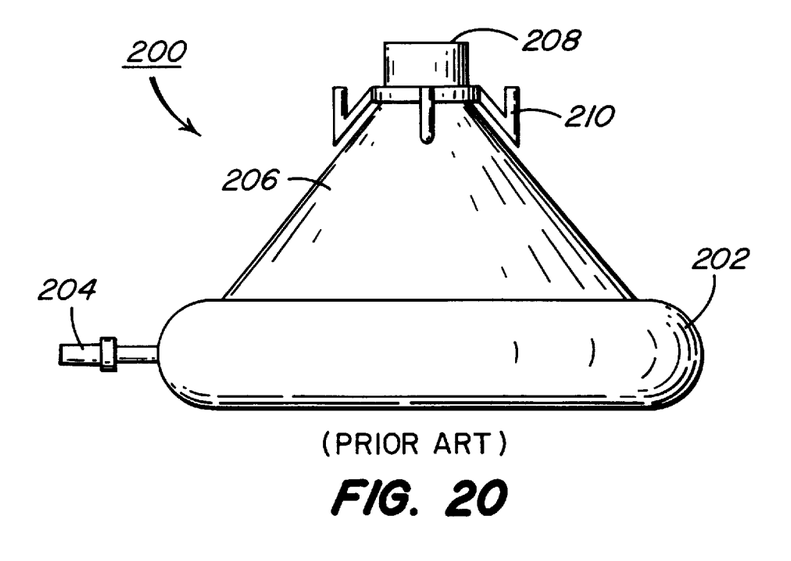
FIG. 20 shows a side view of the airway mask of FIG. 19.

If it becomes necessary during the procedure to provide ventilation to the patient, neither the laryngoscope nor the periscope need be removed from the patient's mouth. A standard airway mask 200, as shown in FIGS. 19 and 20 can fit over the installed laryngoscope and periscope, which, even under a fully retracted position of the laryngoscope, preferably occupies only approximately 10 cm. or less of length outside the patient's mouth and occupies a width, even when combined with the periscope, of preferably no more than 6 cm. The depth is equally minimal, with the proximal end of the periscope extending slightly above the laryngoscope at a height preferably not exceeding 2 cm, and the laryngoscope and periscope combination, which preferably does not exceed 5 cm above the patient's mouth, can fit adequately within the depth of an airway mask. The standard airway mask 200 typically has a length (nose to chin) of 10 cm or greater, width (cheek to cheek) of 8 cm or greater, and depth (opening to opening) of 6 cm or greater, and is thus sized to encompass the present invention when installed. The mask 200 may include an inflatable section 202 with inflation nozzle 204, and a plastic, funnel shaped section 206 tapering to an opening 208 provided with structure 210 for connecting to a ventilation device. The mask 200 is sized to fit snugly over a patients nose and mouth, and to press up against the chin and cheeks. Thus, the prior art laryngoscopic equipment, having long handles, optical equipment, positioning mechanisms, and other exterior apparatus, are not suited for use with such an airway mask, and must be removed prior to ventilation.

Figure 21:
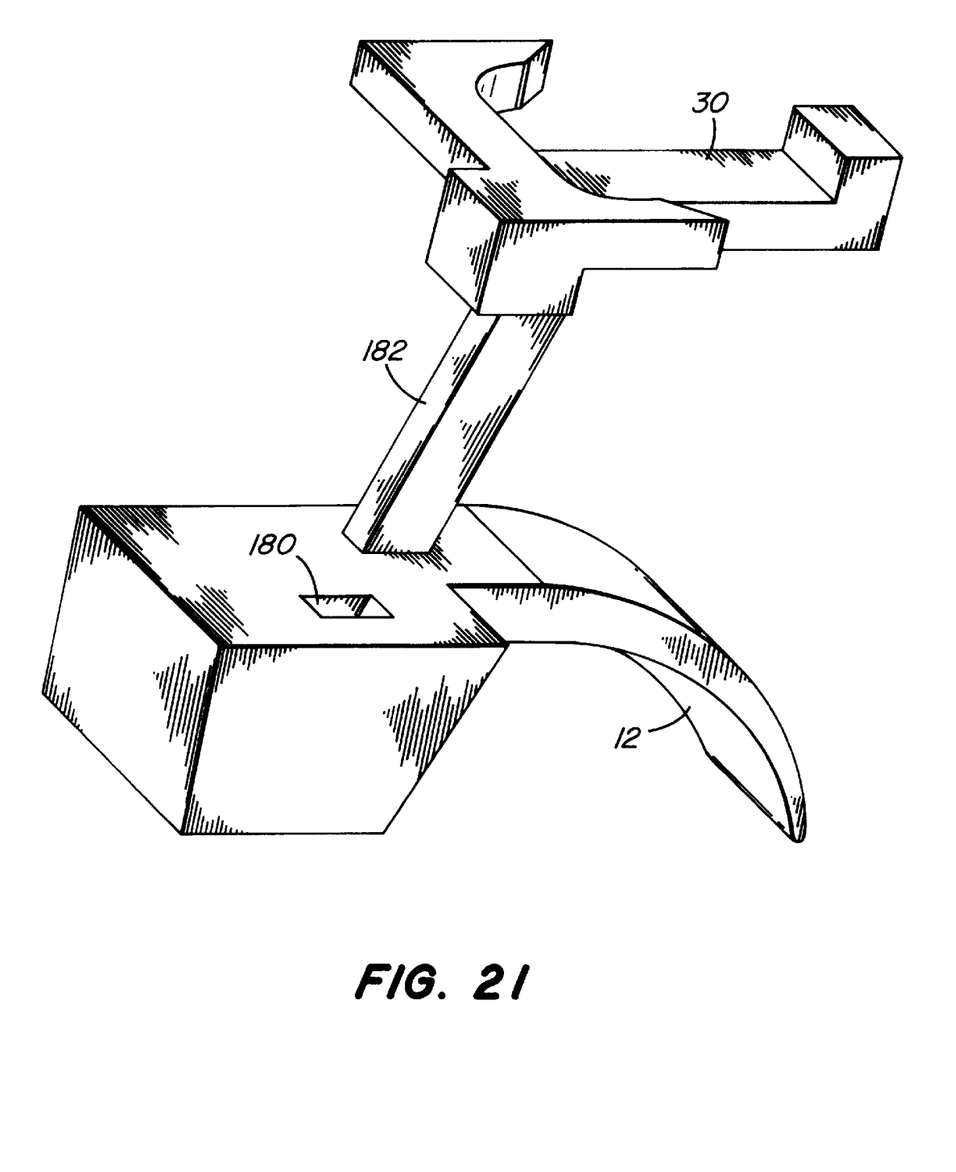
FIG. 21 shows a side perspective view of a retracting laryngoscope with an offset arm shown with blades apart.

Although a central arm connection is preferred to provide the above-described, separate working areas, it is possible to provide the arm connection on the side of the retracting laryngoscope. Thus, it is within the scope of this invention to provide a left or right arm position, as shown, for example, in FIG. 21 which shows an offset arm 182 and an offset opening 180. Further, in such an embodiment, it would be possible to pass the arm through an opening in the straight blade 30 because the patient's nose would not obstruct the arm's movement. In addition, it may, under some circumstances, be desirable to provide multiple arms, such as a pair of evenly spaced arms.

The retracting laryngoscope and periscope of the present invention are preferably made of plastic, which may be injection molded, for economy and disposability. Steel, of course, could be used. A steel product could be provided with disposable plastic protective slip covers which could be thrown away after use to simplify the sterilization procedure. In addition, some parts of the present invention could be made disposable and other parts sterilizable. For example, the retracting laryngoscope could be made from inexpensive, disposable, sturdy plastic while the periscope is made from sterilizable materials and provided with a form-fitting, plastic, protective cover. Furthermore, the device could be comprised of more than the three pieces disclosed. For example, the arm could be separate from both blades (rather than rigidly connected to one of the blades) and the proximal portion of the periscope could snap onto the elongated body of the periscope. Alternatively, the tongue blade portion might be a disposable plastic piece that would snap together with a metal proximal blade housing. In these embodiments, some of the smaller portions could be made disposable. Alternatively, the portions which do not enter the mouth wholly, such as the arm and the proximal end of the periscope could be reusable. Thus, any suitable material is within the scope of this invention, although it is desired that the end product generally be inexpensive. A presterilized periscope and retracting laryngoscope of the present invention could be sold as a kit within a sterilized bag, with or without an endotracheal tube. Different sizes of the periscope and retracting laryngoscope could be made to accommodate the different tissue and mouth sizes of adults and children.

Thus, it is apparent that there has been provided, in accordance with the invention, a periscope and retracting laryngoscope that fully satisfies the objects and advantages set forth above. The periscope and retracting laryngoscope, while in use, are sized to fit under a standard airway mask in any amount of retraction state of the laryngoscope. When the laryngoscope is placed in the mouth, and seated against the lips, the tongue blade is automatically correctly positioned to ensure epiglottic lifting and soft tissue retraction. By manually sliding the two blades apart from each other, the epiglottic lifting and other soft tissue retraction required for tracheal visualization is automatically accomplished via the motion determined by the shape of the arm. Thus, the blade movement can be said to be "pre-programmed" as the proper movement required is accomplished via the arm configuration.

The optics for indirect viewing is separate from the laryngoscope, and can be detachably placed, i.e. can easily and quickly be removed, yet snapped back into exactly the same position for stable, secure, hands-free use. The optics are automatically aimed at the trachea once the periscope is snapped into place. The periscope includes posteriorly placed optics, affording a better view than one-piece laryngoscopes with optics which are anteriorly placed.

The method of using the retracting laryngoscope and periscope provides for the ability to maintain the laryngoscope in a retracted position without having to hold it there. That is, once the laryngoscope is installed, the remainder of the intubation procedure can be performed "hands free" because the operator need not stably hold the laryngoscope in place with one hand while inserting the tube with the other hand.

The method, in addition, "secures" each step of the intubation process, unlike an "attempt" with the prior art wherein the intubator must start over. The present invention incorporates only one "attempt" and once a step is performed, it is "done" (secured) and will not need to be repeated.

While the invention has been described in conjunction with specific embodiments thereof, it is evident that many alternatives, modifications, and variations will be apparent to those skilled in the art in light of the foregoing discussion. For example, it may be possible to provide blades movable relative to one another in ways other than by using the described arms. Accordingly, the present invention is intended to embrace all such alternatives, modifications, and variations as fall within the spirit and broad scope of the appended claims.

What is claimed is:

1. Surgical instrumentation for assisting an intubator in inserting an endotracheal tube into a patient's trachea, the instrumentation comprising:
   a retracting laryngoscope, the laryngoscope comprising a first blade and a second blade, the first and second blades connected by and movable relative to each other by a curved arm which is rigidly connected to one of the first and second blades and which is adapted to movably pass through the other of the first and second blades.

2. The surgical instrumentation of claim 1 wherein the curved arm includes a locking mechanism for selectively maintaining a distance between the first and second blades.

3. The surgical instrumentation of claim 2 wherein the curved arm movably passes through an opening in the first blade, and wherein the curved arm includes a plurality of teeth for engaging within the opening in the first blade.

4. The surgical instrumentation of claim 1 wherein each blade includes a proximal end and a distal end, the curved arm connecting the proximal end of the first blade to the proximal end of the second blade, the proximal end of the second blade further comprising a substantially planar transverse member having a distally facing inner surface adapted to engage upper external oral structures on a patient.

5. The surgical instrumentation of claim 4 wherein the inner surface of the planar transverse member is curved and adapted to provide rotational stability to an inserted laryngoscope.

6. The surgical instrumentation of claim 4 further comprising a block on the distal end of the second blade, the block adapted to engage a roof of a patient's mouth.

7. The surgical instrumentation of claim 1 further comprising a periscope having a distal end and a proximal end, an elongated body connecting the distal end to the proximal end of the periscope, and an angled mirror positioned at the distal end of the periscope, the elongated body and distal end of the periscope sized to fit on one side of the curved arm in a patient's mouth, and the proximal end of the periscope sized to remain on the exterior of the patient's mouth.

8. The surgical instrumentation of claim 7 wherein the periscope and laryngoscope include a detachable snap-on interconnection.

9. The surgical instrumentation of claim 1 wherein the first blade and the second blade abut each other in a closed position and wherein, upon moving the blades along the curved arm towards an open position, the angle between the blades becomes increasingly greater.

10. The surgical instrumentation of claim 9 wherein an angle between the first and second blades at a maximum open position is in the range of 30 degrees to 45 degrees.

11. The surgical instrumentation of claim 10 wherein the radius of curvature of the curved arm is between 3 and 4 inches.

12. A method of visualizing a trachea of a patient for endotracheal intubation, the method comprising the steps of:
   inserting a laryngoscope having a pair of blades into a patient's mouth;
   positioning a distal end of a tongue blade of the laryngoscope into the patient's vallecula; and
   simultaneously lifting the epiglottic tissue and retracting other soft tissue by moving the blades apart by following a path of an arm which connects the pair of blades.

13. The method of claim 12 wherein the step of inserting a laryngoscope comprises inserting a pair of blades into a pharyngeal region of a patient's mouth such that a tongue blade rests upon the patient's tongue and a straight blade abuts a roof of the patient's mouth; the method further comprising the step of pressing a proximal end of each blade against the patient's lips and underlying external oral structures for accomplishing the step of blindly and automatically correctly positioning a distal end of a tongue blade of the laryngoscope in the patient's mouth; the method further comprising the step of moving the blades apart by following a path of an arm which connects the pair of blades for accomplishing the step of blindly and simultaneously lifting the epiglottic tissue and retracting other soft tissue.

14. The method of claim 13 further comprising the steps of placing an airway mask over the laryngoscope and delivering oxygen to the patient.

15. The method of claim 13 wherein the step of moving the blades apart comprises incrementally moving the blades apart, locking the blades with a locking mechanism at a selected increment, and releasing the locking mechanism when further movement of the blades apart or closer together is desired.

16. The method of claim 15 further comprising the steps of
inserting a periscope on one side of the arm;
placing a distal mirror of the periscope in a position which allows for proximal viewing of the trachea;
visualizing the airway from a proximal end of the periscope.

17. The method of claim 16 further comprising the step of snapping the periscope onto the laryngoscope for stability.

18. The method of claim 17 further comprising the steps of detaching the periscope from the laryngoscope and simultaneously leaving the blades in a locked and retracted position within the patient's mouth.

19. Surgical instrumentation for assisting an administrator in an intubation of an endotracheal tube into a patient's airway, the instrumentation comprising:
a retracting laryngoscope, the laryngoscope comprising a first blade and a second blade, the first and second blades connected by and movable relative to each other by an arm which is rigidly connected to one of the first and second blades and which is adapted to movably pass through the other of the first and second blades.

20. The surgical instrumentation of claim 19 further comprising an airway mask, the airway mask having a first opening adapted to press up against the nose and chin of a patient, and a second opening, tapering from the first opening, for attachment to a ventilation device.

21. The surgical instrumentation of claim 19 wherein a combined length of the laryngoscope outside of a patient's mouth in maximum retraction does not exceed 8 cm.

22. The retracting laryngoscope of claim 19 wherein the arm is provided with a radius of curvature between 3 and 4 inches.

23. The retracting laryngoscope of claim 19 wherein the arm is straight and attached to the second blade at an angle between 140 and 150 degrees and wherein the arm, when inserted in an opening in the first blade is at an angle between 30 and 40 degrees to the proxixmal end of the first blade.

24. The surgical instrumentation of claim 19 comprising;
a periscope, the periscope comprising a distal end and a proximal end, an elongated body connecting the distal end to the proximal end of the periscope, and an angled mirror positioned at the distal end of the periscope;
wherein the periscope and the laryngoscope can easily be moved away from each other during an intubation procedure and wherein the periscope and the laryngoscope are sized to fit under a standard airway mask in any state of retraction of the laryngoscope.

25. The surgical instrumentation of claim 24 wherein the periscope and laryngoscope are provided with a snap on connection which detachably and securably connects a proximal section of the periscope to a proximal section of the laryngoscope.

26. The surgical instrumentation of claim 24 wherein a magnifying lens is hingedly connected to the proximal end of the periscope.

27. The surgical instrumentation of claim 24 further comprising a light bulb in the periscope, a switch for the light bulb located at a proximal end of the periscope.

28. The surgical instrumentation of claim 24 wherein the proximal end of the periscope is detachable from the elongated body of the periscope.

29. The surgical instrumentation of claim 24 wherein the angle or direction of the mirror can be altered relative to the elongated body of the periscope.

30. A method of providing ventilation to a patient comprising the steps of:
inserting a laryngoscope into a patient's mouth;
surrounding the laryngoscope and mouth region with an airway mask;
pressing the airway mask onto the patient's face;
providing ventilation through an upper hole in the mask.

31. The method of claim 30 wherein the step of inserting a laryngoscope comprises the step of inserting a pair of blades into a pharyngeal region of a patient's mouth such that a tongue blade rests upon the patient's tongue and an upper blade abuts a roof of the patient's mouth and the step of pressing a proximal end of each blade against the patient's lips, teeth, and other underlying external oral structures.

32. Surgical instrumentation for assisting an intubator in inserting an endotracheal tube into a patient's trachea, the instrumentation comprising:
a first blade on a retracting laryngoscope, the first blade having a proximal block section, a distally facing inner surface on the block section, a tongue pressing surface, a corner point defined by an intersection of the distally facing inner surface on the block section and a lower surface of the tongue pressing surface, and a distalmost point of the tongue pressing surface, wherein a vector relationship exists between the corner point and the distalmost point such that if the corner point defines point (0,0) on an X-Y axis, then the distalmost point defines approximately point (6.5Q,−3Q) where Q=1 for an average adult;
a second blade adapted to abut a roof of a patient's mouth; and,
an arm connecting a proximal end of the first blade to a proximal end of the second blade, wherein the first blade and the second blade may be moved apart or closer together along the arm.

33. A retracting laryngoscope for assisting an intubator in inserting an endotracheal tube into a patient's trachea, comprising:
a first blade;
a second blade;
an arm connecting a proximal end of the first blade to a proximal end of the second blade, wherein the first blade and the second blade may be moved apart or closer together along the arm since the arm is adapted to movably pass through one of the two blades.

* * * * *